United States Patent [19]

Colle et al.

[11] Patent Number: 4,929,631
[45] Date of Patent: May 29, 1990

[54] FUNGICIDE AZOLYL-DERIVATIVES

[75] Inventors: Roberto Colle, Basiglio; Giovanni Camaggi, Novara; Franco Gozzo, San Donato Milanese; Giuseppina Ratti, Seregno; Carlo Garavaglia, Cuggiono; Luigi Mirenna, Milan, all of Italy

[73] Assignee: Agrimont S.r.l., Milan, Italy

[21] Appl. No.: 133,602

[22] Filed: Dec. 16, 1987

[30] Foreign Application Priority Data

Dec. 23, 1986 [IT] Italy ................. 22828 A/86

[51] Int. Cl.$^5$ ................. A01N 43/653; C07D 249/08
[52] U.S. Cl. ................. 514/383; 548/268.6; 548/267.4; 548/267.8
[58] Field of Search ................. 548/262; 514/383

[56] References Cited

U.S. PATENT DOCUMENTS

| | | | |
|---|---|---|---|
| 4,382,944 | 5/1983 | Kramer et al. | 548/262 |
| 4,616,027 | 10/1986 | Richardson et al. | 548/262 |
| 4,661,507 | 4/1987 | Gymer et al. | 548/262 |
| 4,727,159 | 2/1988 | Richardson et al. | 548/262 |

FOREIGN PATENT DOCUMENTS 061835  2/1982  European Pat. Off. ............ 548/262

OTHER PUBLICATIONS

Schaper et al., "Azolyarylalkanol Derivatives, etc." CA 104:5873n (1986).

*Primary Examiner*—Glennon H. Hollrah
*Assistant Examiner*—Patricia L. Morris
*Attorney, Agent, or Firm*—Stevens, Davis, Miller & Mosher

[57] ABSTRACT

Fungicidal compounds having the formula:

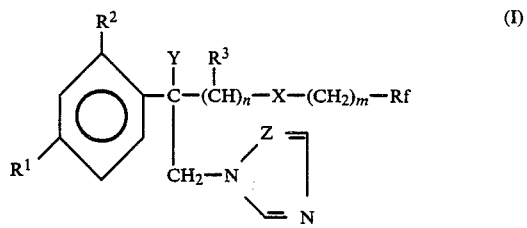

(I)

wherein:
  $R^1$ is selected from the group consisting of F, Cl, Br, CF$_3$, a phenyl, a C$_1$-C$_2$ alkoxy, a C$_1$-C$_2$ haloalkoxy, an alkylthio, and a haloalkylthio radical, in which the halogen is F, Cl, or Br;
  $R^2$ is selected from the group consisting of H, F, Cl, Br, and CF$_3$;
  $R^3$ is H, a C$_1$-C$_4$ alkyl or a C$_3$-C$_6$ cycloalkyl radical;
  Y is selected from the group consisting of H, CH$_3$, OH, CN, and F;
  n is 1, 2, 3, 4 with the proviso that Y is OH when n is 1;
  m is 0 or 1;
  X is O or S;
  Rf is selected from the group consisting of C$_1$-C$_5$ polyfluoroalkyl, C$_2$-C$_4$ polyfluoroalkenyl, polyfluoroalkoxyalkyl and polyfluoroalkoxyalkenyl radicals, each one of them containing at least two fluorine atoms and, optionally, other halogen atoms selected from the group consisting of Cl and Br; and
  Z is CH or N.

5 Claims, No Drawings

FUNGICIDE AZOLYL-DERIVATIVES

FIELD OF THE INVENTION

The present invention relates to azolyl-derivatives having high fungicide and phytogrowth regulating activity, to the process for their preparation and to the corresponding use of such compounds in the agricultural field.

BACKGROUND OF THE INVENTION

From German Patent No. 2,654,890, triazolylcarbinols are known, having general formula:

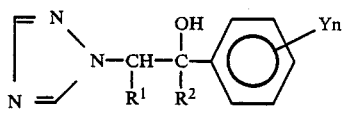

wherein: $R^1$ and $R^2$ are H or a hydrocarbyl group; with the expression hydrocarbyl meaning a saturated or unsaturated, linear or branched chain or a single or condensed ring and, when the hydrocarbyl radical is or contains an aryl group, this latter may be substituted; Y is, for instance, a halogen atom.

From European patent No. 150,036, azolyl-derivatives are also known, having formula:

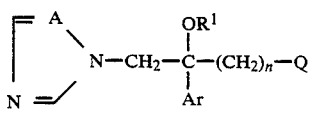

wherein Ar is a substituted aromatic group; A is CH, N; n=2-12; $R^1$=an alkyl, alkenyl, alkynyl or benzyl radical;

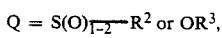

$$Q = S(O)_{\overline{1-2}}-R^2 \text{ or } OR^3,$$

in which $R^2$, $R^3$ are an alkyl, cycloalkyl, alkenyl or aryl radical independently.

Moreover from European patent application No. 145,294 the compounds are known, having formula:

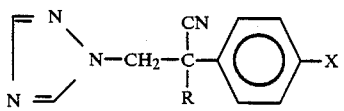

wherein R is a $C_3$–$C_8$ alkyl radical, on condition that, when R is a $C_3$–$C_6$ branched alkyl radical, the branch does not have to be on the alpha carbon atom of group R; X is a halogen atom.

DETAILED DESCRIPTION OF THE INVENTION

We have now found a class of azolyl-derivatives, which differ from the prior art and are endowed with a higher fungicide activity and with phytogrowth regulating properties.

Therefore an object of the present invention concerns the compounds having general formula:

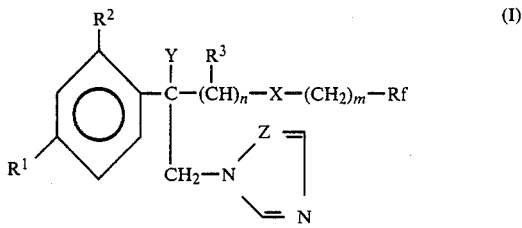

wherein:

$R^1$ is selected from the group comprising F, Cl, Br, $CF_3$, a phenyl, a $C_1$–$C_2$ alkoxy, a $C_1$–$C_2$ haloalkoxy radical, in which the halogen is F, Cl, Br; $R^2$ is selected from the group comprising H, F, Cl, Br, $CF_3$; $R^3$ is H, a $C_1$–$C_4$ alkyl or a $C_3$–$C_6$ cycloalkyl radical; Y is selected from the group comprising H, $CH_3$, OH, CN, F; n is 2, 3, 4 or 1 as well, when Y is OH;

m is 0 or 1;

X is O or S;

Rf is selected from the group consisting of $C_1$–$C_5$ polyfluoroalkyl, $C_2$–$C_4$ polyfluoroalkenyl, polyfluoroalkoxyalkyl and polyfluoroalkoxyalkenyl radicals, everyone of them containing at least two fluorine atoms and, optionally, other halogen atoms selected from Cl and Br; Z is CH or N.

The compounds having general formula (I) are endowed, as mentioned above, with a higher fungicide activity and with phytogrowth regulating properties and may be used advantageously in agricultural, medical and veterinary fields.

The compounds of the present invention contain at least a chiral centre and are generally obtained in the form of racemic mixtures.

The single enantiomers can be separated from these mixtures by methods, known in literature.

Both the single enantiomers and the possible diastereoisomers or geometric isomers, generated by several chiral centres or by possible double bonds, form an object of the present invention.

The following compounds form also an object of the present invention:

the salts of the compounds having formula (I) coming from an inorganic acid such as hydrohalogenic acid, for instance hydroiodic, hydrobromic, hydrochloric acid; sulphuric, nitric, thiocyanic and phosphoric acid: or from an organic acid such as acetic, propanoic, ethanedionic, propanedionic, benzoic, methanesulphonic, 4-methylbenzenesulphonic acid and the like;

the metal complexes obtained by complexation reaction between the derivatives of type (I) with an inorganic or organic metal salt such as halogenide, nitrate, sulphate, phosphate of, for instance, copper, manganese, zinc or iron.

The compounds having formula (I) of the present invention can be obtained by different process according to the value of n, m and Y.

(1) A general process for the preparation of the compounds having formula (I), when m is O, consists in carrying out an addition reaction of the compounds having formula:

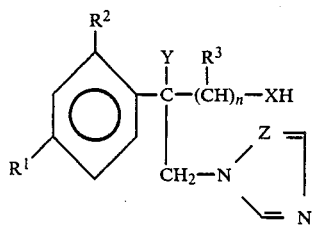

(II)

wherein $R^1$, $R^2$, $R^3$, Y, X and Z have the meanings, as specified hereinbefore, to a fluoroolefin having formula:

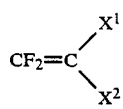

wherein $X^1$ is F, Cl, $CF_3$; $X^2$ is F, Cl, $CF_3$ or $OX^3$, which $X^3$/a polyfluoroalkyl radical having from 1 to 3 carbon atoms, containing at least three fluorine atoms and optionally other halogen atoms selected from Cl and Br, in the presence of aprotic solvents, such as, for instance, DMF, DMSO, THF, dioxane or pyridine, or in an alcoholic solvent, such as, for instance terbutanol, in the presence of catalytic or stoichiometric amounts of a strong organic or inorganic base, such as, for instance, sodium hydride, potassium terbutilate and potassium hydroxide, at temperatures ranging from $-20°$ C. to $100°$ C., to yield the compounds having formula:

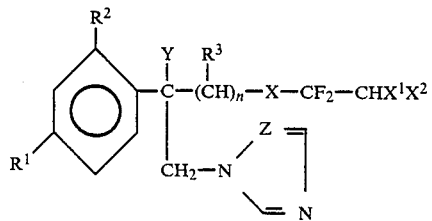

(Ia)

By subsequent dehydrofluorination reaction of the compounds of formula (Ia), which reaction may also take place spontaneously during the above described reaction, an unsaturation may be introduced in the α-position of group Rf, thereby obtaining the unsaturated compounds having formula:

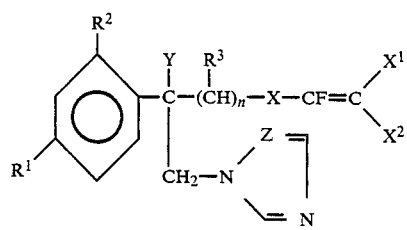

(Ib)

(2) Another process for the preparation of the compounds having formula (I), when X is O and is 1, consists in carrying out a reaction of nucleophil substitution on the reactive ester having formula:

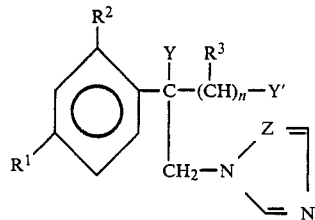

(III)

wherein Y' represents a halogen atom or a mesyl or tosyl group, by means of an alkaline salt of a polyfluorinated alcohol of formula (IV), according to the reaction scheme:

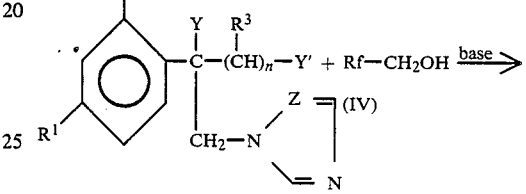

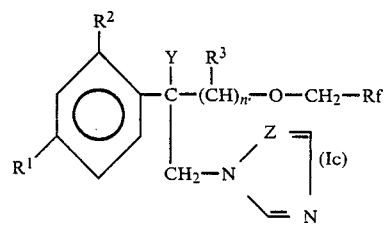

(Ic)

The reaction is carried out preferably in aprotic dipolar solvents, such as DMF, DMSO or ethereal solvents, such as, for instance, diethylether, THF or dioxane, in the presence of stoichiometric amounts of a strong base, such as, for instance, sodium hydride or potassium terbutylate. The reactive ester of formula (III) can be obtained easily, by treating the corresponding primary alcohol of formula (II), wherein X is O, with a halogenation, tosylation or mesylation agent.

(3) Another process for the preparation of the compounds having formula (I), when m is O, consists in reacting an alkaline salt of a compound of formula (II) with a polyfluoro-alkyl-halogenide having formula:

Rf-$X^4$, in which $X^4$ is a halogen atom, such as chlorine, bromine or fluorine, according to the reaction scheme:

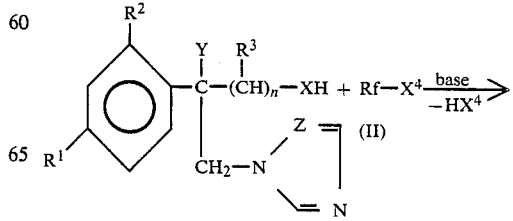

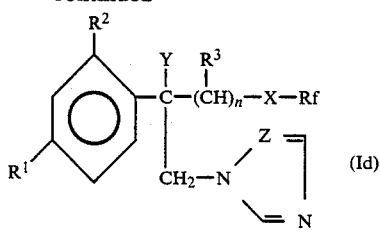

The reaction is carried out in conditions similar to the ones indicated hereinbefore for process (2).

(4) Another process for the preparation of the compounds having formula (I), when Y is —OH, consists in reacting a polyfluorinated oxirane of formula (XI) with an alkaline salt of an azole, according to the reaction scheme:

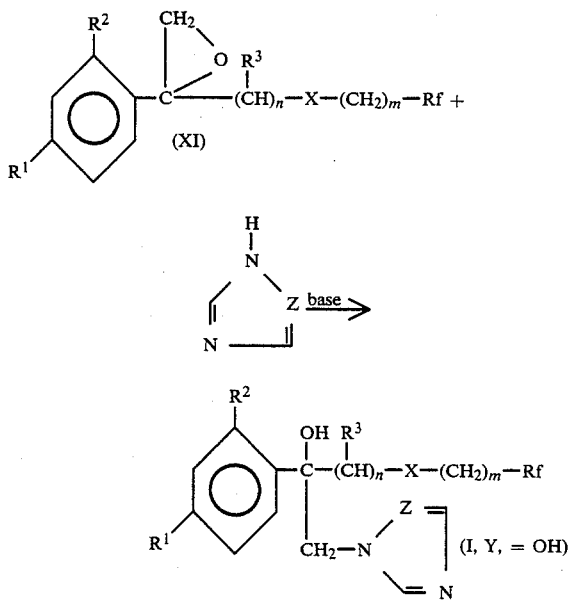

The reaction is generally carried out in an aprotic dipolar solvent, such as DMSO or DMF, in the presence of stoichiometric amounts of a strong base, such as sodium hydride, potassium terbutylate or KOH, at temperatures ranging from the room temperature to the reflux temperature of the solvent.

The intermediate compounds of formula (II), when $R^3$ is H, employed in processes (1) and (3), may be prepared by reduction of the esters having formula:

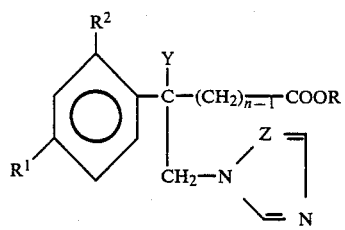

wherein $R^1$, $R^2$, Y and Z have the meanings, as specified hereinbefore and R represents an ethyl or a methyl radical, by using mixed hydrides, such as, for instance, LiAlH$_4$, LiBH$_4$, NaBH$_4$, in solvents of ethereal kind, such as, for instance, diethylether, THF, at temperatures ranging from 0° C. to 30° C.

The intermediate compounds of formula (V) can, in their turn, be prepared by different methods, according to the nature of Y and the value of n.

(a) When Y=OH the intermediate compounds of formula (V) can be prepared by conversion of the compounds having formula (VI) into the corresponding oxiranes of formula (VII) and subsequent conversion of the oxiranes of formula (VII) into carbinols (V) (Y=OH), by reaction with an alkaline salt of azole, according the reaction schemes:

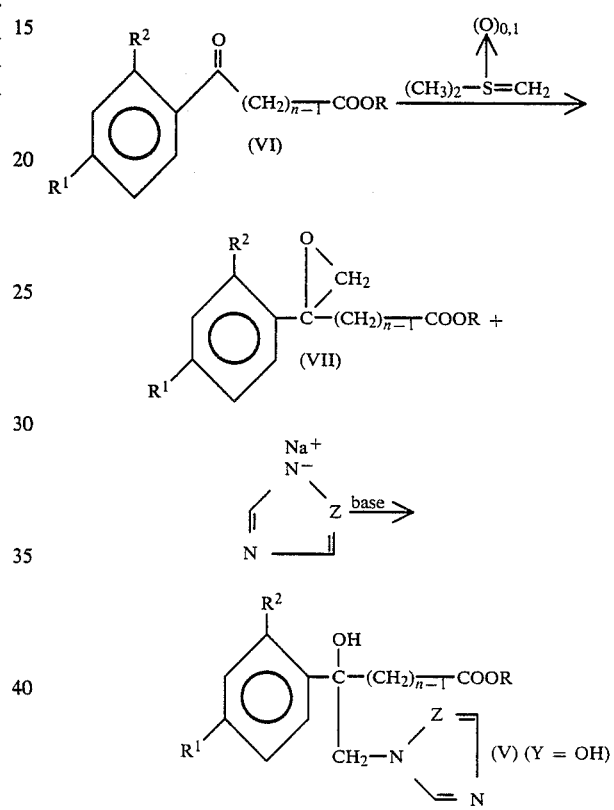

The compounds having formula (VI) are known in the prior art, for instance, from: Kindler, Metzendorf, Chem. Berichte 76 (1943) 308; Johnson, J. C. S. (1946)895; Jur'ev et al., 2, obšč. chim. 24 (1954)1568; Dauben, Tilles, J. Org. Chem. 15 (1950)785; Bertachio, Dreux, Bulletin Soc. Chim. Fr. (1962)823.

The conversion reaction of compounds (VI) into oxiranes (VII) is carried out according to a known methodology, for instance from:

Corey, Chaykovsky, J.A.C.S. 87 (1965)1353 and J.A.C.S. 84 (1962)3782.

The conversion reaction of oxiranes (VII) into carbinols (V), is generally carried out, in an aprotic dipolar solvent, such as, for instance, DMSO or DMF, in the presence of stoichiometric amounts of a strong base, such as sodium hydride, potassium terbutylate or potassium hydroxide, at temperatures ranging from the room temperature and the reflux temperature of the solvent.

(b) When Y=OH and n=1, the intermediate compounds of formula (V) can be prepared by subjecting to alcoholysis the cyanhydrines having formula (VIII) according to the reaction

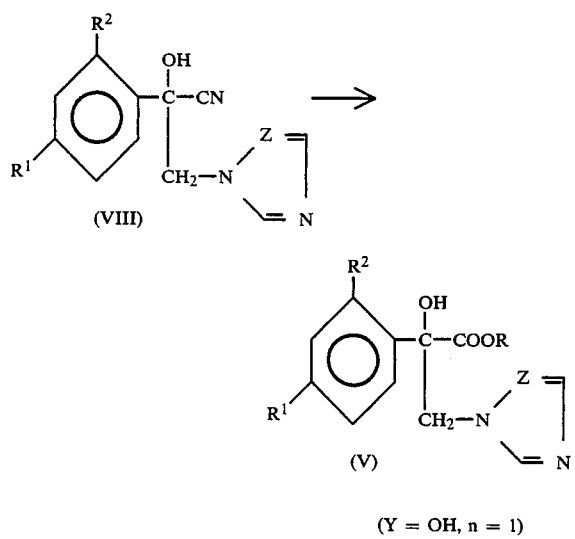

(Y = OH, n = 1)

The alcoholysis reaction is generally carried out in an alcoholic solvent, such as ethanol or methanol, saturated with gaseous HCl, or in the presence of another mineral acid, such as sulphuric acid, at temperatures ranging from 0° C. to the boiling point of the solvent.

The cyanohydrides of formula (VIII) can, in their turn, be prepared by addition of HCN to the suitable azolylacetophenones or starting from nitryls of formula (X), known, for instance, from Dreux, Regeand, Bull. Soc. Chem. Fr. (1959)1244, through the following set of reactions:

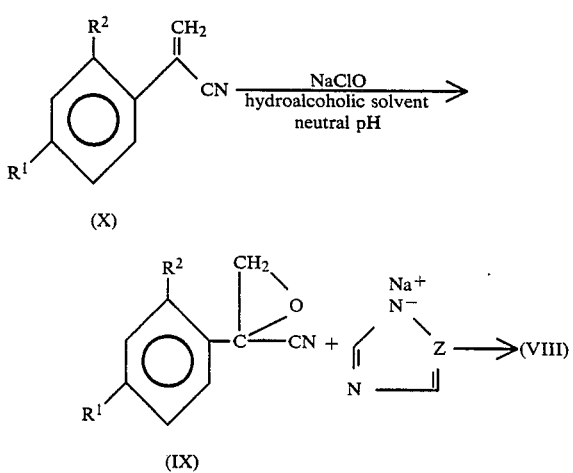

(c) When Y is different from OH, the intermediate compounds of formula (V) can be prepared by known methods, for instance, when Y=CN, they can be prepared from nitryls having formula:

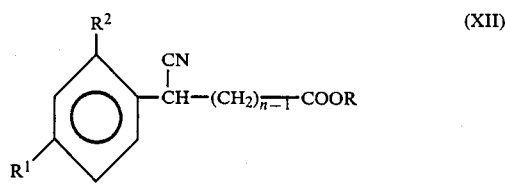

by hydroxymethylation in the alpha position with respect to nitryl, by means of bases and formaldehyde, followed by mesylation and displacement of mesylate by means of an alkaline salt of azole.

(d) When Y=F, the intermediate compounds of formula (V) can be prepared from carbinols of formula (V), wherein Y=OH, by treatment with diethylaminosulfotrifluoride (DAST), in an inert solvent, such as, for instance $CH_2Cl_2$, at temperatures ranging from −70° C. to 0° C.

Another method for preparing the compounds of formula (II), when Y=H, consists in dehydrating the compounds of formula (V), wherein Y=OH and subsequently in hydrogenating catalytically the resultant olefin.

The intermediate oxiranes of formula (XI), when $R^3$ is H, used in process (4) can be prepared by reacting ketones (XIII) with a sulfonium halide or sulfoxonium hylide, by using a methodology known, for instance, from Corey, Chaykovsky, J.A.C.S. 87 (1965)1353 and J.A.C.S. 84 (1962)3782, according to the reaction scheme:

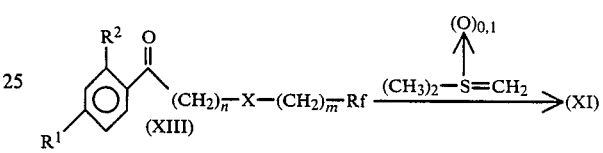

The ketones of formula (XIII) can, in their turn, be prepared by Friedel-Kraft condensation, starting from acid chlorides of formula (XIV), according to the following reaction:

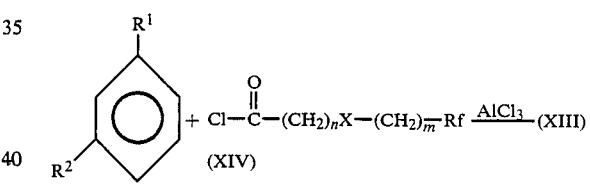

This reaction, already known, is carried out by using as solvent the same benzenic derivative, used as starting compound at temperatures ranging from the room temperature and the boiling temperature of the mixture.

For the synthesis of the acid chlorides having formula (XIV), it is convenient to start from a ω-hydroxy (or mercapto) ester of formula (XV), afterwards, by following the reaction scheme previously described with methods (1), (2) and (3) for the preparation of the compounds of formula (I), fluorinated esters (XVI) are obtained.

The esters of formula (XVI), thus obtained, are then hydrolyzed, in an alkaline aqueous medium, to yield the corresponding acids (XVII), that, in their turn, are converted into the acid chlorides of formula (XIV), by a chlorination agent, for instance thionyl chloride, optionally in the presence of a catalyst, such as DMF, at temperatures ranging from 20° to 60° C., according to the reaction schemes:

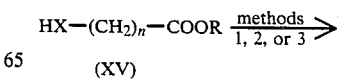

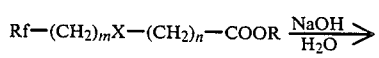

-continued

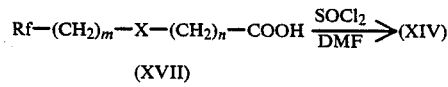

In particular, the compounds of formula (XVI), when m=O and Rf=$X^1X^2$CH—$CF_2$—, in which $X^1$ and $X^2$ have the meanings, as specified hereinbefore, are prepared by reacting esters (XV) with a fluoroolefin having formula:

$CF_2$=$CX^1X^2$, in the presence of aprotic solvents, such as for instance, DMF, DMSO, THF, dioxane or pyridine, or in an alcoholic solvent, such as for instance terbutanol, in the presence of catalytic or stoichiometric amounts of a strong organic or inorganic base, such as, for instance, sodium hydride, potassium terbutylate, at temperatures ranging from −20° C. to 100° C., according to the reaction scheme:

HX—$(CH_2)_n$—COOR + $CF_2$=$CX^1X^2$ $\xrightarrow{\text{base}}$ (XV)

$X^1X^2$CH—$CF_2$—X—$(CH_2)_n$—COOR (XVI a)

Examples of compounds having general formula (I), according to the present invention, are reported in Table 1.

TABLE 1

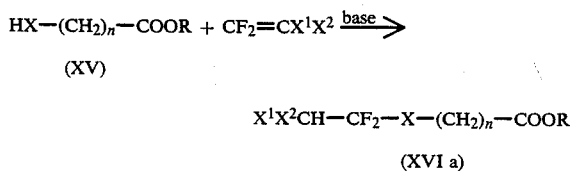

(I)

| compound N. | Y | $R^1$ | $R^3$ | $R^2$ | Z | X | n | m | Rf |
|---|---|---|---|---|---|---|---|---|---|
| 1 | —OH | Cl | H | Cl | N | O | 1 | 0 | —$CF_2$—$CF_2H$ |
| 2 | —OH | Cl | H | Cl | N | O | 2 | 0 | —$CF_2$—$CF_2H$ |

The compounds having general formula (I) are endowed with fungicide activity and phytogrowth regulating activity and may be used advantageously both in agricultural field and in the medical-veterinary one.

Their fungicide activity proves to be particularly high against phytopathogenous fungi infesting cereal cultivations, fruit-growing, industrial and horticultural cultivations.

Examples of plant diseases that can be fought by using the compounds of the present inventions are the following ones:

*Erysiphe graminis* on cereals
*Sphaeroteca fuliginea* on cucurbitaceae (for inst. cucumber)
*Puccinia*, on cereals
*Septoria* on cereals
*Helminthosporium* on cereals
*Rhynchosporium* on cereals
*Podosphaera leucotricha* on apple-trees
*Uncinula necator* on vines
*Venturia inaequals* on apple-trees
*Piricularia oryzae* on rice
*Botrytis cinerea*
*Fusarium* on cereals
and still other deseases.

Moreover the compounds of formula (I) possess other positive characteristics, such as a fungicide action having both curative and preventive character and a complete compatibility towards the plants, which have to be protected against the fungus infection.

Besides the high fungicide activity, due to preventive and curative applications, the compounds of formula (I) are characterized by systemic properties.

These properties permit the products to enter the vascular systems and to act even in sits (for instance leaves), that are very far away from the ones they have been applied in (for instance, roots).

For the practical uses in agriculture, it is often advantageous to make use of fungicide compositions containing one or more compounds of formula (I) as active substance.

The application of these compositions can take place on every part of the plant, for instance, leaves, stalks, branches and roots or on the seeds themselves, before the sowing, or on the soil adjoining the plant as well. The compositions may be used, in the form of dry powders, wettable powders, emulsifiable concentrates, pastes, granulates, soluttions, suspensions and the like: the choice of the kind of composition will depend on the specific use. The compositions are prepared, according to a known way, for instance, by diluting or dissolving the active substance by means of a solvent medium and/or a solid diluent, optionally in the presence of surfactants. The following compounds may be used as solid diluents or carriers: silica, kaolin, bentonite, talc, diatomite, dolomite, calcium carbonate, magnesia, gypsum, clays, synthetic silicates, attapulgite, sepiolite. Besides of course, water, several kinds of solvents may be used as liquid diluents, for instance, aromatic solvents (benzene, xylenes, or mixtures of alkylbenzenes), chloroaromatic solvents (chlorobenzene), paraffins (oil cuts), alcohols (methanol, pro-panol, butanol), amines, amides (dimethylformamide), ketones (cyclohexanone, acetophenone, isophorone, ethyl-amylketone), esters (isobutylacetate). As surfactants may be used: sodium salt, calcium salts or triethanolamine of alkylsulfates, alkylsulfonates, alkyl-arylsulfonates, polyethoxylated alkylphenols, fatty alcohols condensed with ethylene oxide, polyoxyethylated fatty acids, pooxyethylated sorbitol esters, polyoxyethylated fats, ligninsulfonates. The compositions may also contain special additives for particular purposes, for instance adhesive agents such as gum-arabic, polyvinyl alcohol, polyvinylpyrrolidone.

If desired, other compatible active substances may be also added to the compositions, object of the present invention, such as fungicides, phytodrugs, phytogrowth regulators, herbicides, insecticides, fertilizers.

The concentration of active substance in the aforesaid compositions can vary within a wide range, according to the active compound, the cultivation, the pathogen, environmental conditions and the kind of formulation, that has been used. The concentration of active substance generally ranges from 0.1 to 95, preferably from 0.5 to 90% by weight.

The invention will now be illustrated by the following examples.

EXAMPLE 1

Preparation of 1-(1,2,4-triazolyl)-2-hydroxy-2-(2,4-dichlorophenyl)-4-(1,1,2,2-tetrafluoroethoxy)butane (compound No 2).

Potassium terbutylate (0.2 g) was added to 1-(1,2,4-triazolyl)-2-(2,4-dichlorophenyl)-2,4-dihydroxy-butane (1.9 g) dissolved in anhydrous THF (10 ml), anhydrous DMSO (20 ml), anhydrous terbutanol (20 ml), in a nitrogen atmosphere, at $-10°$ C.

After having produced the vacuum in the apparatus, tetrafluoroethylene was introduced there and the whole was maintained in an atmosphere of this gas overnight, at room temperature.

Then the reaction mixture was poured into water and extracted by means of ethyl acetate.

The extract was washed with water, dried on anhydrous sodium sulfate and evaporated. The crude product thus obtained, was analyzed by silica gel chromatography, by eluting with 1:1 n-hexane-ethyl acetate.

0.8 g of a whitish solid were isolated, having a melting point of $70°-71°$ C., which was characterized as being in keeping with the structure indicated in the title, on the ground of the following spectroscopic data.

I.R. ($\nu$, cm$^{-1}$) 3150, 1590, 1520, 1280, 1200, 1120, N.M.R. $^1$H (90 MHz) TMS in CDCl$_3$, $\delta$: 2.10–2.45 (m, 1H); 2.55–2.95 (m, 1H); 3.80–4.30 (m, 2H); 4.55 (d, 1H); 5.20 (d, 1H); 5.20 (s, 1H); 5.60 (tt, 1H); 7.30 (dd, 1H); 7.40 (m, 1H); 7.75 (d, 1H); 7.90 (s, 1H); 8.10 (s, 1H).

EXAMPLE 2

Preparation of 1-(1,2,4-triazolyl)-2-hydroxy-2-(2,4-dichlorophenyl)-3-(1,1,2,2-tetrafluoroethoxy)-propane (compound No 1).

This compound was prepared by a process similar to the one described in example 1, starting from 1-(1,2,4-triazolyl)-2-(2,4-dichlorophenyl)-2,3-dihydroxy-propane.

The compound was characterized by the following spectroscopic data.

NMR $^1$H (60 MHz) TMS in CDCl$_3$ $\delta$: 4.10 (s. broad, 2H); 4.85 (s. broad, 2H) 5.10 (s, 1H); 5.55 (tt, 1H); 7.35–7.70 (m, 3H); 7.90 (s, 1H); 8.10 (s, 1H).

EXAMPLE 3

Determination of the fungicide activity against cucumber oidium (*Sphaerotheca fuliginea* (Schlech) Salmon).

Preventive activity:

Cucumber plants c.v. Marketer, grown in pots in a conditioned environment, were sprayed on their lower leaf faces with the product being tested in a water-acetone solution, containing 20% of acetone (vol./vol.). Then the plants were kept in a conditioned environment for 1 day, afterwards they were sprayed on their upper leaf faces with an aqueous suspension of conidia of *Sphaerotheca fuliginea* (200,000 conidia/ml). The plants were then carried back to a conditioned environment.

At the end of the incubation period of the fungus (8 days) the infection degree was valued according to indexes of a valuation scale ranging from 100 (=sound plant) to 0 (=completely infected plant).

Curative activity:

Cucumber plants cv. Marketer, grown in a conditioned environment, were sprayed on their upper leaf faces with an aqueous suspension of conidia of *Sphaerotheca fuliginea* (200,000 conidia/ml.). 24 hours after the infection the plants were treated with the products being tested in a water-acetone solution containing 20% of acetone (vol./vol.) by spraying both leaf faces.

At the end of the incubation period of the fungus (8 days), during which time the plants were kept a suitably conditioned environment, the infection degree was valued according to indixes of a valuation scale ranging from 100 (=sound plant) to 0 (=completely infected plant).

The results are recorded in Table 2.

EXAMPLE 4

Determination of the fungicide activity against wheat oidium (*Erysiphe Graminis D.C.*).

Preventive activity:

Leaves of wheat cv. Irnerio, grown in pots in a conditioned environment, were treated, by spraying both leaf faces with the products being tested, in a water-acetone solution containing 20% of acetone (vol./vol.).

After a stay time of 1 day in a conditioned environment at 20° C. and 70% of relative humidity, the plants were sprayed on both leaf faces with an aqueous suspension of Erysiphe Graminis (200,000 conidia/cc.). After a stay time of 24 hours in an environment saturated with moisture, at 21° C., the plants were kept in a conditioned environment for the fungus incubation.

At the end of said period of time (12 days), the infection degree was valued according to indexes of a scale ranging from 100 (sound plant) to 0 (completely infected plant).

Curative activity:

Leaves of wheat cv. Irnerio, grown in pots in a conditioned environment, were sprayed on both leaf faces with an aqueous suspension of Erysiphe Graminis (200,000 conidia/cc). After a stay time of 24 hours in an environment saturated with moisture, at 21° C., the leaves were treated with the products being tested, in a water acetone solution containing 20% of acetone (vol/vol), by spraying both leaf faces.

At the end of the incubation period (12 days), the infection degree was valued at sight, according to indixes of a valuation scale ranging from 100 (=sound plant) to 0 (=completely infected plant).

The results are recorded in Table 2.

EXAMPLE 5

Determination of the fungicide activity against wheat linear rust (*Puccinia Graminis Pers.*)

Preventive activity:

Leaves of wheat cv. Irnerio, grown in pots in a conditioned environment, were treated by spraying both leaf faces with the products being tested in an aqueous water-acetone solution containing 20% of acetone (vol./vol). After a stay time of 1 day in a conditioned environment, at 23° C. and 70% of relative humidity, the plants were sprayed on both leaf faces with a mixture of spores of *Puccinia Graminis* in talc (100 mg of spores/5 mg of talc).

After a stay time of 48 hours in an environment saturated with moisture, at 21° C., the plants were kept in a conditioned environment for the fungus incubation.

At the end of said period of time (14 days), the infection degree was valued at sight, according to indexes of a scale ranging from 100 (sound plant) to 0 (completely infected plant).

Curative activity:

Leaves of wheat cv. Irnerio, grown in pots in a conditioned environment, were sprayed on both leaf faces with a mixture of spores of *Puccinia Graminis* in talc (100 mg of spores/5 mg of talc); after a stay time of 48 hours in an environment saturated with moisture, at 21° C., the leaves were treated with the products being tested in a water-acetone solution containing 20% of acetone (vol/vol), by spraying both leaf faces.

At the end of the incubation period (14 days) the infection degree was valued at sight, according to indexes of a valuation scale ranging from 100 (=sound plant) to 0 (completely infected plant).

The results are recorded in Table 2.

EXAMPLE 6

Determination of the fungicide activity against apple-tree Ticchiolatura (*Venturia inaequalis* (*CKe*) *Wint*).

Preventive activity:

Leaves of apple-trees cv. Starking, grown in pots in a glasshouse, were treated by spraying both leaf faces with the products being tested, in a water-acetone solution containing 20% of acetone (vol/vol). After a stay time of 1 day in a conditioned environment, at 20° C. and 79% of relative humidity, the plants were sprayed uniformly with an aqueous suspension of conidia of *Venturia inaequalis* (200,000 conidia/cc). After a stay time of 2 days in an environment saturated with moisture, at 21° C., the plants were kept in a conditioned environment for the fungus incubation.

At the end of this period (14 days) the infection degree was valued at sight, according to indexes of a valuation scale ranging from 100 (sound plant) to 0 (completely infected plant).

Curative activity:

Leaves of apple-trees cv. Starking, grown in pots in a glasshouse, were sprayed uniformly with an aqueous suspension of conidia of *Venturia inaequalis* (200,000 conidia/cc); after a stay time of 2 days in an environment saturated with moisture said leaves were treated with the products being tested, in a water-acetone slution containing 20% of acetone (vol/vol), by spraying both leaf faces. At the end of the incubation period (14 days) the infection degree was valued at sight, according to indexes of a valuation scale ranging from 100 (sound plant) to 0 completely infected plant).

The results are recorded in Table 2.

We claim:

1. The compounds having the formula:

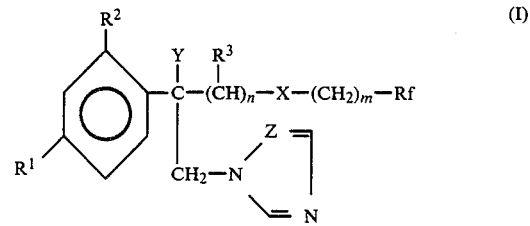

wherein:

$R^1$ is selected from the group consisting of F, Cl, Br, $CF_3$, a phenyl, a $C_1$–$C_2$ alkoxy, and a $C_1$–$C_2$ haloalkoxy, radical, in which the halogen is F, Cl, or Br;

$R^2$ is selected from the group consisting of H, F, Cl, Br, and $CF_3$;

$R^3$ is H, a $C_1$–$C_4$ alkyl or a $C_3$–$C_6$ cycloalkyl radical;

Y is OH;

n is 1, 2, 3, 4 with the proviso that Y can only be OH when n is 1;

m is 0 or 1;

X is O or S;

$R_f$ is selected from the group consisting of $C_1$–$C_5$ polyfluoroalkyl and $C_2$–$C_4$ polyfluoroalkenyl radicals, each of these containing at least two fluorine atoms and Z is N.

2. A compound according to claim 1 which is 1-(1,2,4-triazolyl)-2-hydroxy-2-(2,4-dichlorophenyl)4-(1,1,2,2-tetrafluoroethoxy) butane.

3. A compound according to claim 1 which is 1-(1,2,4-triazolyl)-2-hydroxy-2-(2,4-dichlorophenyl)-3-(1,1,2,2-tetrafluoroethoxy)propane.

4. Fungicide compositions having as active ingredient an effective amount of at least one compound according to claims 1, 2 or 3, together with an inert solid or liquid carrier.

5. A method of controlling fungus infections in useful plants consisting in distributing on the plant or in the area adjoining the plant, when the fungus infection is foreseen or when it is already in progress, an effective amount of at least one compound according to claims 1, 2 or 3, either as such or in the form of a suitable composition.

TABLE 2

| Compound No. | Dose g/l | *Sphaerotheca fuliginea*/cucumber | | *Erysiphe graminis trit.*/wheat | | *Puccinia graminis*/wheat | | *Venturia inaequalis*/apple-tree | |
|---|---|---|---|---|---|---|---|---|---|
| | | Preventive activity | Curative activity | Preventive activity | Curative activity | Preventive activity | Curative activity | Preventive activity | Curative activity |
| 1 | 0.5 | 100 | 100 | 100 | 100 | 100 | 100 | 100 | 100 |
| | 0.25 | 100 | 100 | 100 | 100 | 100 | 100 | 100 | 100 |
| | 0.125 | 100 | 100 | 100 | 100 | 100 | 100 | 100 | 100 |
| 2 | 0.5 | 100 | 100 | 100 | 100 | 100 | 100 | 100 | 100 |
| | 0.25 | 100 | 100 | 100 | 100 | 100 | 100 | 100 | 100 |
| | 0.125 | 100 | 100 | 100 | 100 | 100 | 100 | 100 | 100 |